United States Patent [19]

Hurley

[11] 4,319,045

[45] Mar. 9, 1982

[54] PROCESS FOR PRODUCTION OF A TARTRONIC ACID SOLUTION

[75] Inventor: Rupert B. Hurley, Williamsburg, Va.

[73] Assignee: Badische Corporation, Williamsburg, Va.

[21] Appl. No.: 240,749

[22] Filed: Mar. 5, 1981

[51] Int. Cl.³ .................... C07C 59/245; C07C 59/06
[52] U.S. Cl. .................... 562/582; 562/597; 562/585
[58] Field of Search .................... 562/582, 585, 597

[56] References Cited

U.S. PATENT DOCUMENTS 3,488,385  1/1970  Marangoni et al. ............... 562/582

FOREIGN PATENT DOCUMENTS 46-11323  3/1971  Japan ................................. 562/582

*Primary Examiner*—Paul J. Killos
*Attorney, Agent, or Firm*—Rupert B. Hurley, Jr.

[57] ABSTRACT

The invention disclosed herein describes a process of making a solution of tartronic acid. The tartronic acid solution was produced by a controlled oxidation reaction employing potassium permanganate, and one of several starting materials.

7 Claims, No Drawings

PROCESS FOR PRODUCTION OF A TARTRONIC ACID SOLUTION

BACKGROUND OF THE INVENTION

1. Field of the Invention

This invention pertains to the production of a specific acyclic carboxylic acid, namely a particular oxypolycarboxylic acid known as tartronic acid. Any of several starting materials is consecutively reduced, oxidized, precipitated, filtered, and redissolved in order to produce a solution of tartronic acid. Reaction conditions are critical in the process disclosed.

2. Description of the Prior Art

The closest prior art reference known to the applicant is A. Lachman, J. American Chemical Society, 1921, 43,577. Lachman discloses a process of producing tartronic acid by dissolving tartaric acid in nitric acid and adding sulfuric acid to the mixture, resulting in the formation of nitrotartaric acid which was then hydrolyzed to form tartronic acid, among other products. Even though tartaric acid is conceived to be a member of the group of starting materials of the present invention, the present invention does not include and is not comprehended by the treatment of tartaric acid with nitric acid or any other acid. No patent literature has been found to be as relevant to the present invention as the Lachman reference.

3. Brief Summary of the Invention

The present invention pertains to a process of producing tartronic acid. In the process of the present invention, a starting material is converted to its salt form and is then oxidized at low temperature and under basic conditions. The salt is oxidized to oxalic acid (the major product) and tartronic acid (a minor product). Based upon 100% conversions of starting material to tartronic acid, the maximum yield of tartronic acid obtained by the process of the present invention has been approximately 20%.

DETAILED DESCRIPTION OF THE PREFERRED EMBODIMENTS

It is conceived that the starting materials used in carrying out the process of the present invention include any one or more of the members of the group consisting of: maleic acid, fumaric acid, tartaric acid, maleic acid anhydride, tartaric acid anhydride, or any of the water soluble esters of maleic acid, fumaric acid, or tartaric acid.

The starting material is first converted to an aqueous salt solution having a pH between 10 and 14, more preferably a salt solution having a pH between 12.0 and 13.5. The starting material is converted into a salt by adding the starting material to water, followed by the addition of a base (e.g. sodium hydroxide) to the solution until the pH increases to between 10 and 14. Most preferably base is added until the solution has a pH between 12.0 and 13.5. At this point the starting material has been converted into a salt of the diacid. An alternative (equivalent) conversion of the starting material may be carried out by dissolving a water soluble salt of the starting material. Base is then added to this aqueous solution. The base is added until the pH of the solution is between 10 and 14 (or, as above, preferably between 12.0 and 13.5).

The basic salt solution is next cooled to a temperature between the freezing point of the salt solution and 25° C. More preferably the basic salt solution is cooled to between its freezing point and 15° C. Most preferably the basic salt solution is cooled to between its freezing point and 5°–10° C. While maintaining this low temperature, a solution of potassium permanganate is slowly added to the cold basic salt solution, while stirring. Potassium permanganate is added to the salt solution until the molar ratio of permanganate to salt is between 1.5 and 2.5. Most preferably the molar ratio is between 1.8 and 2.1. The oxidation reaction between the organic salt and potassium permanganate is exothermic, necessitating the removal of heat from the system during the reaction in order to keep the reactants and products from heating up during the reaction.

It has been found that heating the reactants during the oxidation reaction will result in an increased rate and degree of oxidation which results in an increased degree of formation of oxalic acid, hence heating of the reactants is undesireable. A precipitate, herein defined as the first precipitate, formed from the reaction between potassium permanganate and the organic salt. The solution containing the reaction products was filtered after the first precipitate was allowed to settle. The reaction products remaining in solution were determined to include oxalic acid and tartronic acid.

The separation of oxalic acid and tartronic acid was accomplished by precipitating the acids quantitatively followed by selective dissolution of the tartronic acid. A water soluble salt which formed oxalates which were insoluble in both acidic and basic media and which formed tartronates soluble in acidic but insoluble in basic media was utilized in separating the oxalic acid from the tartronic acid. The salt used was zinc chloride, and it is conceived that any water soluble zinc salt whose anion does not attack tartronic acid or oxalic acid would be operable in the process of the present invention. It has been further conceived that any water soluble salt capable of forming oxalates in soluble in acidic and basic media while forming tartronates which are insoluble in a basic media but soluble in acidic media would be operable in the process of the present invention. Enough salt was added to the oxidation reaction products to essentially complete the precipitation of the oxalic acid and tartronic acid.

The water soluble salt was added to the solution containing the oxidation reaction products. Both the oxalic acid and the tartronic acid formed insoluble salts which precipitated, this precipitate herein defined as the second precipitate. The second precipitate was removed from the solution via filtration, and was added to a solution which contained a mineral acid, causing the tartronate to selectively redissolve. The redissolved tartronic acid was filtered after the remaining precipitate was allowed to settle. The decanted solution containing tartronic acid also contained the cation of the water soluble salt, which was zinc in the case where zinc chloride was selected as the water soluble salt. The mineral acid used to acidify the solution containing the zinc oxalate and zinc tartronate was hydrochloric acid, although sulfuric acid and nitric acid are also conceived to be operable in the process of the present invention.

The tartronic acid solution was used as described in U.S. Pat. No. 4,029,725, column 2, 11. 34–48. It is further conceived that the tartronic acid may be isolated for uses as described in the prior art. Means for separation of the tartronic acid from the zinc cation is conceived to be known to those having skill in the art.

EXAMPLE

Twenty pounds of maleic anhydride was added to 15–20 gallons of water to produce a maleic anhydride solution. Eighty pounds of a 50% NaOH solution was then slowly added to the maleic anhydride solution. During the addition of NaOH the temperature of the reactants and products was not allowed to exceed 60°–65° C. The reaction between the NaOH and maleic anhydride resulted in the formation of a highly basic maleic anhydride salt solution.

Sixty-three pounds of $KMnO_4$ were added to sixty-two liters of water to produce a permanganate solution.

The highly basic maleic acid salt solution was cooled to 5°–10° C. and small amounts of the permanganate solution (prepared supra) were slowly added. The temperature of the reactants and products was not allowed to exceed 15° C. (cooling coils were used in cooling). The reaction mixture was stirred. After the reaction was completed, a first precipitate, $MnO_2$, was allowed to settle to the bottom of the reactant vessel. The first supernate, a highly basic solution containing oxidation products, were filtered in order to separate the supernate from the precipitate. The precipitate, $MnO_2$, was discarded.

The highly basic solution containing oxidation products was heated to 35°–38° C., and a concentrated solution of $ZnCl_2$ was added to the highly basic solution until the pH was lowered to $10\pm0.2$, in order to precipitate the tartronate ion and the oxalate ion. A second precipitate formed in the bottom of the reaction vessel, which was comprised of insoluble salts of oxidation products, i.e. oxalates and tartronates. After the precipitate settled a second supernate was filtered off and discarded.

Concentrated hydrochloric acid, between 70 and 100 pounds, was added to the second precipitate to lower the pH to $0\pm0.2$. The HCl addition was monitored to prevent the solution from having a negative pH. The solution was stirred and the remaining portion of the second precipitate was allowed to settle. A third supernate was filtered and saved while the remaining portion of the second precipitate was discarded. The third supernate was a highly acidified solution of tartronic acid, the solution also containing zinc cation.

What is claimed is:

1. A process of producing a tartronic acid solution, comprising the steps of: p1 (a) converting a starting material into a salt, so that the resulting salt solution has a pH between 10 and 14, wherein the starting material is a member selected from a group consisting of maleic acid, fumaric acid, tartaric acid, maleic acid anhydride, tartaric acid anhydride, a water soluble ester of maleic acid, a water soluble ester of fumaric acid, a water soluble ester of tartaric acid;
    (b) oxidizing the salt solution with aqueous $KMnO_4$ at a pH of at least 10 and a temperature between the freezing point of the salt solution and 25° C., with the molar ratio of $KMnO_4$ to salt being between 1.5 and 2.5;
    (c) removing a first precipitate from the oxidized salt solution;
    (d) adding a water soluble salt to the solution until the precipitation of the oxalate and tartronate are complete, wherein the water soluble salt is a member selected from the group of water soluble salts whose oxalates and tartronates are insoluble in base, whose oxalates are insoluble in acid, and whose tartronates are soluble in acid;
    (e) separating off a second precipitate resulting from the addition of the metal salt;
    (f) dissolving the tartronate by adding a mineral acid to the second precipitate.

2. A process as described in claim 1 wherein the salt solution is oxidized with $KMnO_4$ at a temperature between the freezing point of the salt solution and 15° C.

3. A process as described in claim 2 wherein the molar ratio of $KMnO_4$ to salt is between 1.8 and 2.1.

4. A process as described in claim 3 wherein the oxidation of the salt solution is carried out on a salt solution having a pH between 12 and 13.5.

5. A process as described in claim 4 wherein the starting material is maleic acid anhydride.

6. A process as described in claim 5 wherein the water soluble salt is a zinc salt whose anion is non-attacking.

7. A process as described in claim 6 wherein the water soluble salt is zinc chloride.

* * * * *